United States Patent
Silvano et al.

(10) Patent No.: US 8,567,949 B2
(45) Date of Patent: Oct. 29, 2013

(54) OPHTHALMIC DEVICE AND METHOD

(75) Inventors: Pieri Silvano, Florence (IT); Simone Spadini, Florence (IT); Francesco Versaci, Prato (IT); Gabriele Vestri, Florence (IT)

(73) Assignee: Costruzioni Strumenti Oftalmici C.S.O. S.R.L., Scandicci (Firenze) (IT)

( * ) Notice: Subject to any disclaimer, the term of this patent is extended or adjusted under 35 U.S.C. 154(b) by 195 days.

(21) Appl. No.: 13/190,039

(22) Filed: Jul. 25, 2011

(65) Prior Publication Data
US 2012/0033180 A1 Feb. 9, 2012

(30) Foreign Application Priority Data
Aug. 5, 2010 (IT) .................. FI2010A0173

(51) Int. Cl.
 *A61B 3/14* (2006.01)
 *A61B 3/10* (2006.01)
(52) U.S. Cl.
 USPC ............ 351/210; 351/209; 351/212; 351/246
(58) Field of Classification Search
 USPC ......................................... 351/208–210, 212
 See application file for complete search history.

(56) References Cited

U.S. PATENT DOCUMENTS

| | | | |
|---|---|---|---|
| 5,870,167 A | 2/1999 | Knopp et al. | |
| 7,712,899 B2 | 5/2010 | Tanassi et al. | |
| 7,771,050 B2* | 8/2010 | Honda et al. | 351/208 |
| 2004/0116811 A1* | 6/2004 | Koschmieder | 600/452 |
| 2005/0174536 A1* | 8/2005 | Hanaki et al. | 351/205 |
| 2009/0207376 A1 | 8/2009 | Nakashima et al. | |
| 2011/0001930 A1* | 1/2011 | Levecq | 351/209 |
| 2012/0062842 A1* | 3/2012 | Griggio et al. | 351/209 |

FOREIGN PATENT DOCUMENTS

| | | |
|---|---|---|
| EP | 0933060 | 8/1999 |
| EP | 1430829 | 6/2004 |

OTHER PUBLICATIONS

European Search Report for FI20100173 filed on Mar. 29, 2011 in the name of Costruzioni Strumenti Oftalmici C.S.O. S.R.I.
Written Opinion for FI20100173 filed on Aug. 5, 2010 in the name of Costruzioni Strumenti Oftalmici C.S.O. S.R.I.

* cited by examiner

*Primary Examiner* — Jordan Schwartz
(74) *Attorney, Agent, or Firm* — Steinfl & Bruno LLP

(57) ABSTRACT

An ophthalmic device and method actively correcting possible movement of the eye of a patient with respect to the correct positioning during the examination are described. An illumination light beam is provided, that passes through a cross-section of the anterior chamber of the eye to capture an image on the corneal vertex.

12 Claims, 3 Drawing Sheets

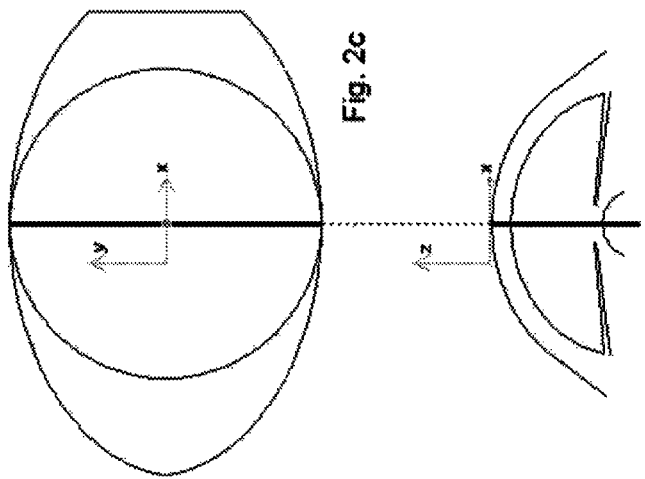
Fig. 2c
Fig. 3c
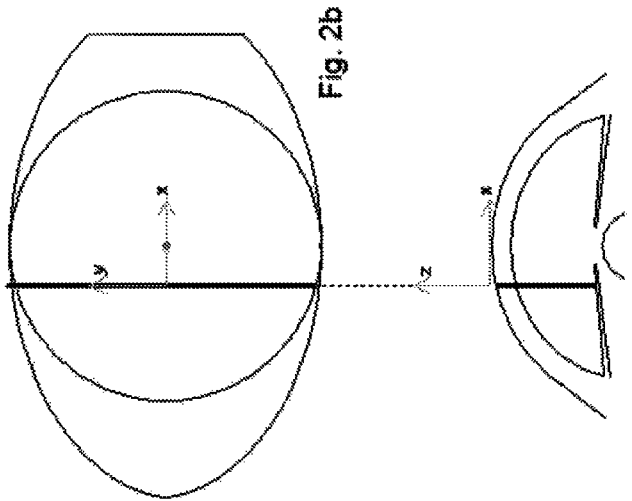
Fig. 2b
Fig. 3b
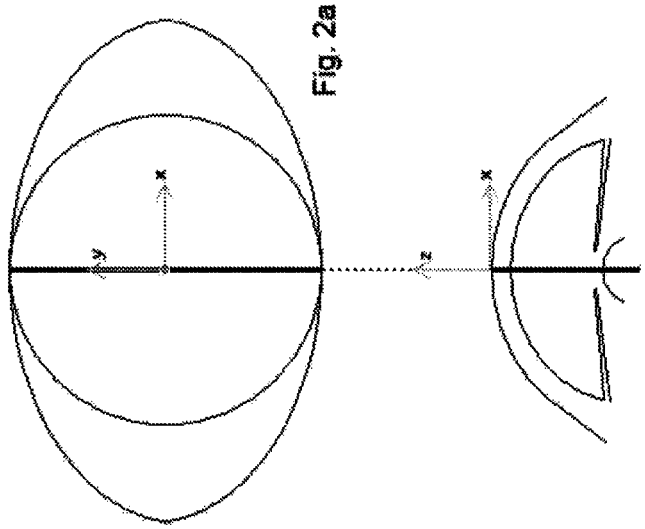
Fig. 2a
Fig. 3a

OPHTHALMIC DEVICE AND METHOD

CROSS REFERENCE TO RELATED APPLICATIONS

The present application claims priority to Italian patent application FI2010A000173 filed on Aug. 5, 2010, which is incorporated herein by reference in its entirety.

FIELD

The present disclosure is related to ophthalmic devices and methods, and in particular devices and methods for analysing the cornea and/or the anterior segment of the eye.

BACKGROUND

Over the last few years a series of ophthalmic devices of the aforementioned type have been developed, based upon a slit illumination of a section of the cornea and upon the recording of such an illuminated section through a suitable observation system. Most of such devices capture and record images of various sections of the eye, through rotation of the capturing devices around the optical axis of the eye and, through suitable processing, they obtain a three-dimensional reconstruction of the anterior chamber of the same eye.

One of the main problems that has been experienced when using this kind of devices is that the eyes of the patient, however cooperative and concentrated he may be on correctly fixing the fixation point provided by the device, cannot keep absolutely still. On the other hand the scanning of the eye requires a certain period of time in order to be completed. Therefore, what occurs is that during the rotating scanning, the ideal position for capturing the eye becomes misaligned with respect to the rotation axis of the capturing device. This misalignment, when positioning the single sections with respect to one another and therefore in the three-dimensional reconstruction phase of the anterior chamber, can lead to artefacts and considerable errors.

In order to solve this problem, different "a posteriori" correction methods have been proposed and implemented in devices that are currently on the market. An example of such a way to approach the problem is provided by the device described in EP1430829. Indeed, a specific functional solution forms the object of such a patent, that is, simultaneously recording sectional images and front images, the latter showing an image of the illuminated sectional portion of the cornea, so as to make it possible to assign a section captured at a time T to the area that is indeed illuminated, formed by the front image.

This second solution has the following drawbacks:
saving the image twice (from the front and from the side) means an extra functional workload of the examination and an increase in the computational costs;
compensation a posteriori, in any case, does not offer a completely satisfactory solution, since it is necessary for there to be a mathematical interpolation of the data when assigning them to their position again, and an interpolation is of course less reliable than a direct data measurement.

Active correction solutions are also known. For example, U.S. Pat. No. 7,712,899 describes a solution with two perpendicular channels for simultaneously recording two sections of the eye and a third video observation channel, that is capable of detecting the possible misalignment of the eye and the consequent correction through the movement of a considerable part of the two recording systems of the sections.

A system of this kind however, in turn, is structurally and operatively complex, and therefore its practical application comes up against constructive problems, control difficulties and inaccuracy of the results.

SUMMARY

According to an aspect of the present disclosure, a method and a measuring device are provided, that solve the problem of misalignment of the eye of the patient during the examination in a more satisfactory manner, in terms of simplification and reduction of the examination costs and of accuracy of the results, with respect to known systems that follow an a posteriori approach, like the one mentioned above for instance, or others that, again within such a generic approach, adopt alternative solutions.

According to a further aspect of the present disclosure, a method and a device of the aforementioned type are provided, which adopt an active or pre-emptive correction system that is reliable, constructively and functionally simple.

According to another aspect, an ophthalmologic device for capturing and/or measuring features of an anterior chamber of an eye of a patient is provided, the device comprising: a first light projection system adapted to illuminate a cross-section of the anterior chamber under examination with an illumination light beam along a relevant optical axis; a capturing system adapted to observe an image of the cross-section of the anterior chamber illuminated by said first light projection system in a correct capturing position; a second light projection system adapted to generate a fixation light beam determining a fixation point for the eye of the patient as a reference for said correct capturing position; and detection and control means comprising: a mobile optical member adapted to interfere at least with said illumination beam and, with its motion, to displace the beam; sensor means adapted to detect a movement of the eye with respect to said correct positioning; and a control unit adapted to control, as a response to the detection by said sensor means, the operation of said mobile optical member to displace said beam towards said correct capturing position.

According to still another aspect, a method for capturing images and/or measuring features of an anterior chamber of an eye of a patient is provided, comprising: illuminating a cross-section of the anterior chamber under examination with an illumination light beam of a first light projection system along a relevant optical axis; observing with a capturing system an image of the cross-section of the anterior chamber illuminated by said illumination light beam in a correct capturing position; and generating with a second light projection system a fixation beam determining a fixation point for the eye of the patient as a reference for said correct capturing position, wherein a mobile optical member interferes at least with said illumination beam, a movement of the eye with respect to said correct position is detected, and in response to the detection the operation of said mobile optical member is controlled to displace said beam towards a correct capturing position.

A first light projection system creates a flat blade of light, which passes through a cross-section of the anterior chamber of the eye under examination. This light is diffused by the eye structures it meets, and can be observed by a capturing or acquisition system arranged at a certain angle with respect to the plane of the blade of light. The capturing system forms a focused image on the sensor that records the section of the anterior chamber crossed by the blade of light.

The patient is required to fix a fixation point, consisting of a collimated beam generated by a second illumination and projection system. The aforementioned blade of light of the first light projection system is parallel to the fixation beam.

The movements of the eye are detected through reading the image of the collimated fixing beam reflected by the cornea, by an electro-optical detection element.

A mobile optical member, inserted in the common path of the blade of light of the first light projection system, of the collimated beam of the second light projection system and of the reflected image of the cornea, allows for a controlled translation of the same blade, and of the other beams, in a direction that is perpendicular to the lying plane of the same beam.

The possible movements of the eye of the patient, with respect to the device, lead to its displacement away from the ideal position, said position being that in which the blade of light passes through the corneal vertex. The measurement system quantitatively defines the amount of such a movement. In response to this measurement the mobile optical member, crossed by the beams, is moved of an amount suitable in order to displace the blade of light to the position passing through the corneal vertex. In these conditions, also the reflected image of the cornea is re-aligned on the corneal vertex.

According to embodiments of the present disclosure, the misalignment of the eye of the patient is actively corrected by bringing the blade of light back to the corneal vertex, in the case in which, when capturing a frame, the position of the patient is not correct.

BRIEF DESCRIPTION OF THE DRAWINGS

Further characteristics of the ophthalmic device and method according to the present disclosure shall become clearer from the following description of one of its embodiments, given as an example and not for limiting purposes, with reference to the attached drawings, in which:

FIGS. 2a, 3a, 2b, 3b, 2c and 3c represent pairs of views of the eye under examination, each pair including a front view and a section view, respectively in three different situations of (mis)alignment of the eye and of translation of the blade of light for illuminating the same eye.

DETAILED DESCRIPTION

Figure 1A:
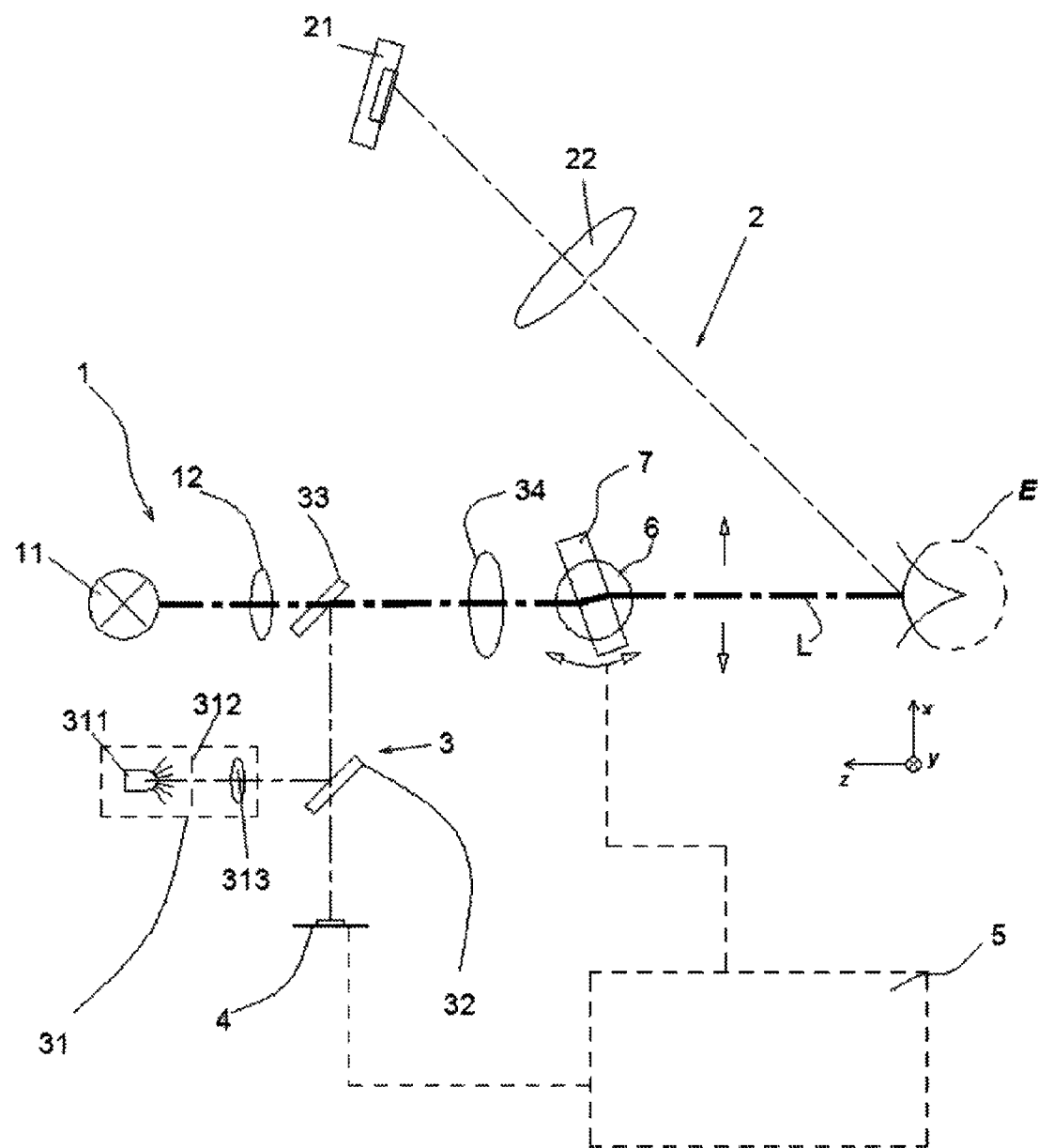
FIGS. 1a and 1b represent an example diagram of the device for analysing the anterior segment of the eye in which, in FIG. 1a, the optical path of the illumination is marked from the source to the eye and, in FIG. 1b, the optical path of the fixation point from the source to the eye and of the reverse path of the image reflected by the cornea are marked.
Figure 1B:
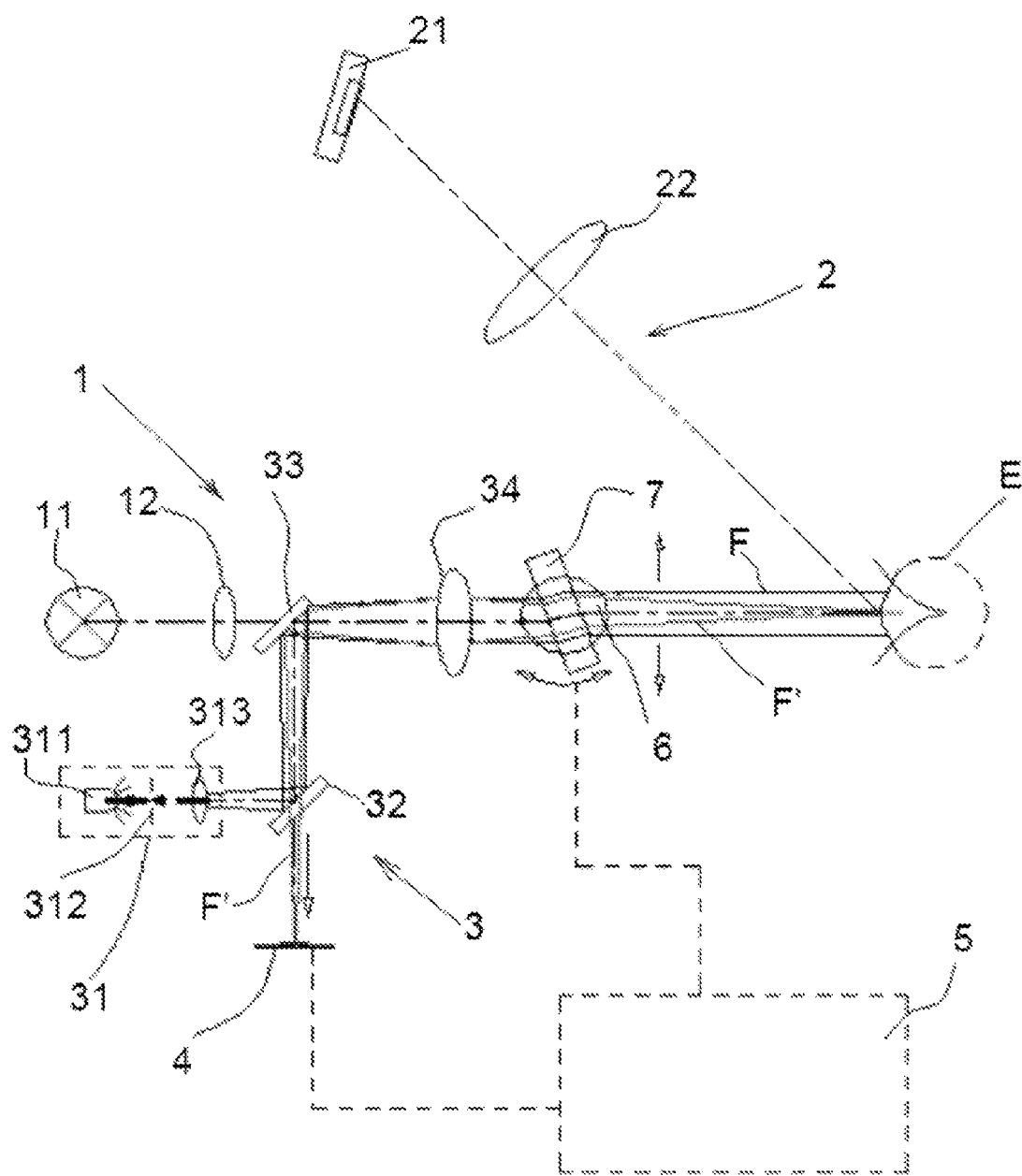

With reference to FIGS. 1a and 1b, in an embodiment of the device according to the present disclosure an illuminator 11 frontally illuminates, in a first light projection system wholly indicated with reference numeral 1 and that can be defined as central, an eye E of a patient, and in particular the relative anterior chamber so as to highlight a section thereof.

The central optical system comprises an optical group 12 such as to make the light emission of the illuminator 11—at the correct capturing distance that can be determined according to known optic principles—a blade of light L (FIG. 1a).

A capturing system 2 is arranged outside the central projection beam in a way such as to focus, on an image capturing device 21 thereof, typically a CCD sensor, the section illuminated by the central optical system 1, and in particular by the illuminator 11. The sensor 21 observes the section of the cornea from a position outside the blade of light generated by the illuminator 11 and can be arranged, for example, according to a Scheimpflug configuration.

A light source 311 generates a luminous fixing point and projects it towards the eye E through a second light projection system to obtain a collimated light beam F, in a way such as to be perceived to infinity by the patient. Such a system, wholly indicated with reference numeral 3, comprises a diaphragm 312, a group of lenses 313, all integrated with the source 311 in a fixing device 31 which—as such—can be considered as conventional. The fixing device 31 is arranged so as to obtain a projection that is parallel to the projection of the first system 1.

The second light projection system 3 further comprises a pair of beam deviators or beam splitters 32, 33, the first of which, indicated with reference numeral 32, deviates the projection of the fixing device onto an optical axis of the second light projection system, sideways or, like in the example, perpendicular to the first optical axis. The second beam splitter 33 is arranged on the optical axis of the first system, so as to deviate the projection of the fixing device 31 along such first optical axis, downstream of the previously mentioned optical element 12, and cooperates with other optical elements 34, arranged further downstream, i.e. towards the eye E, suitable for achieving the desired collimation (FIG. 1b).

As a constructional fixed parameter, the blade of light generated by the illuminator 11 of the first central system lies on a plane that is parallel to the direction of the collimated fixing beam generated by the fixing device 31. Consequently, when the eye E is positioned correctly for the imaging capture on the plane xy (i.e. plane tangent to the eye at the point of incidence of the central optical axis, see the reference Cartesian coordinate system indicated in FIG. 1a), the image point of such a fixation beam, reflected by the cornea, lies on the plane of the blade of light.

A detector 4, typically in the form of a matrix of electro-optical sensors 4, is associated with the second light projection system, along the relative lateral optical axis, so as to be adapted to detect the position of an image, reflected by the cornea, of the collimated fixing beam, generated as mentioned by the fixing device 31, and therefore in turn deviated by the above described components. The reflected beam is represented with a lighter line, with respect to that of the collimated beam, in FIG. 1b.

A processing and control unit 5 comprises processing means suitable for receiving and processing the digital signal detected by the detector 4, i.e. a signal representative of the position of the reflected image of the collimated beam on the cornea of the eye E. A man skilled in the art will appreciate that such a result can be obtained both by a digital-based processing and by analogue control means. The processing unit 5 is also suitable for emitting a control signal of an actuator 6, the actuation of which drives a mobile optical member 7 arranged so as to intersect the blade of light, the collimated fixation beam and the corresponding collimated image of the cornea, so as to be able to displace the blade of light and to keep it centred in the position of the corneal vertex, actively compensating for voluntary or involuntary movements of the eye of the patient.

In a possible embodiment such a mobile optical member 7, placed between the first and second light projection system 1, 3 and the eye E, can be made up of a simple parallel flat transparent lamina pivoting (as indicated by the arrows) around an axis that is parallel with the plane xy and with the lying plane of the blade of light L. Therefore, in practice, this rotation axis is in accordance with the direction defined by the axis indicated with y in FIG. 1a. The lamina, when its faces are perpendicular to the blade of light (nominal position), does not alter the optical path thereof. On the other hand, by tilting the lamina 7 with respect to the nominal position, the blade of light that illuminates the eye is translated by an amount depending on the tilt angle (again see the arrows of FIG. 1a). It should moreover be noted that such a tilting of the lamina 7 does not modify the direction of the collimated fixation beam projected by the fixing device 31, which is thus perceived always in the same direction by the patient. From the point of view of the sensor 4, on the other hand, the movement of the blade of light caused by the tilting of the lamina 7 is perceived (reflection F' in FIG. 1b) as an opposite movement of the image of the reflection of the collimated fixation beam. When such a reflection lies on the plane of the blade of light, its image on the sensor 4 is in a position that is univocally determined and represents the position of correct alignment.

The processing and control unit 5, based upon the error detected by the sensor 4, thus drives the tilting of the lamina 7 so that such an error is made null, obtaining, in such a way, the aforementioned alignment. In practice, the error is made null when, thanks to the prismatic effect of the lamina 7, the reflection of the fixation point F' has returned to the centre of the sensor 4 and with it the blade of light L has returned to strike the cornea at its vertex. Such a control procedure can of course be run with a software that is obviously implemented on the unit 5.

In order to better and further understand how the device according to the present disclosure works, reference will now be made to the situations shown in FIGS. 2 and 3 (a, b, c).

In FIGS. 2a and 3a the ideal situation is shown in which the eye is aligned, the reflection of the fixation point is aligned with the corneal vertex, the plane of the blade of light passes through the corneal vertex. In this case the processing and control unit 5 can keep the lamina 7 in the nominal condition.

In FIGS. 2b and 3b a non-ideal situation is shown in which the eye is not aligned properly, the reflection of the fixation point is displaced from the corneal vertex by a certain amount, and the plane of the blade of light does not pass through the corneal vertex if the lamina 7 is kept in the nominal position. Such a situation is detected thanks to the sensor 4 and acquired by the unit 5. In response, to displace the blade of light, so that it goes back to the corneal vertex, it is necessary for the unit 5 to tilt the lamina 7 by a certain angle. In FIGS. 2c and 3c the situation in which this occurs is shown. At this stage, the illuminated ocular section is the desired one, that is, the section passing through the corneal vertex, even if the eye is misaligned (misalignment that can be noted from the displacement with respect to the origin of the Cartesian system represented in the figure sand taken as a reference).

The present disclosure has been described thus far with reference to its possible example embodiments. It should be understood that other embodiments can is make use of optical configurations that, though arranged differently from those here shown and integrated with additional components/functions, are within the scope of protection of the following claims.

The invention claimed is:

1. An ophthalmologic device for capturing and/or measuring features of an anterior chamber of an eye of a patient, comprising:
   a first light projection system adapted to illuminate a cross-section of the anterior chamber under examination with an illumination light beam along a relevant optical axis;
   a capturing system adapted to observe an image of the cross-section of the anterior chamber illuminated by said first light projection system in a correct capturing position;
   a second light projection system adapted to generate a fixation light beam determining a fixation point for the eye of the patient as a reference for said correct capturing position; and
   detection and control means comprising:
      a mobile optical member, disposed along only a portion of said illumination light beam, adapted to interfere at least with said illumination beam and, with its motion, to displace the beam;
      sensor means adapted to detect a movement of the eye with respect to said correct positioning; and
      a control unit adapted to control, as a response to the detection by said sensor means, the operation of said mobile optical member to displace said beam towards said correct capturing position, wherein
      the mobile optical member is a transparent, substantially planar lamina, pivotally supported and driven by actuator means controlled by a control unit.

2. The device according to claim 1, wherein said sensor means of said detection and control means are adapted to detect a reflection of said fixation beam by said anterior chamber, said control unit being adapted to control the operation of said optical mobile element based on a displacement of said reflection detected by said sensor means.

3. The device according to claim 1, wherein said lamina is adapted to tilt around a rotation axis parallel with the tangent plane to the eye at the point of incidence of the optical axis of said first light projection system.

4. The device according to claim 3, wherein said first light projection system is adapted to generate an illumination beam, said rotation axis of said lamina being parallel to the lying plane of said illumination light beam.

5. The device according to claim 1, wherein said second light projection system is adapted to generate a collimated light beam along a portion of said optical axis of said first light projection system, and comprises optical deviation means arranged between a portion of said optical axis of said first system and a lateral optical axis interfering with said sensor means.

6. The device according to claim 1, wherein said capturing system is arranged in a Scheimpflug configuration with respect to said first light projection system.

7. A method for capturing images and/or measuring features of an anterior chamber of an eye of a patient, comprising:
   illuminating a cross-section of the anterior chamber under examination with an illumination light beam of a first light projection system along a relevant optical axis;
   observing with a capturing system an image of the cross-section of the anterior chamber illuminated by said illumination light beam in a correct capturing position; and
   generating with a second light projection system a fixation beam determining a fixation point for the eye of the patient as a reference for said correct capturing position,
   wherein a mobile optical member, disposed along only a portion of said illumination light beam, interferes at least with said illumination light beam, a movement of the eye with respect to said correct position is detected, and in response to the detection the operation of said mobile optical member is controlled to displace said beam towards a correct capturing position, wherein said mobile optical member is a transparent, substantially planar, pivotally supported lamina.

8. The method according to claim 7, wherein at least a reflection of said fixation beam by said anterior chamber of the eye is detected, the operation of said mobile optical member being controlled based on the detection of a displacement of said reflection.

9. The method according to claim 7, wherein said lamina is pivoted around a rotation axis parallel to the tangent to the eye at the point of incidence of the optical axis of said first light projection system.

10. The method according to claim 9, wherein said first light projection system generates an illumination light beam, the rotation axis of said lamina being parallel to the lying plane of said illumination light beam.

11. The method according to claim 7, wherein said second light projection system generates a collimated light beam along a portion of said optical axis of said first light projection system, an optical deviation being arranged between a portion of said optical axis of said first system and a lateral optical axis along which said detection is carried out.

12. The method according to claim 7, wherein said capturing system is arranged in a Scheimpflug configuration with respect to said first light projection system.

* * * * *